United States Patent [19]
Ancher et al.

[11] Patent Number: 4,459,296
[45] Date of Patent: Jul. 10, 1984

[54] PIPERAZINES AND HOMOPIPERAZINES, N-SUBSTITUTED BY AN AROMATIC HETEROCYCLIC GROUP, AND THEIR USE IN THERAPEUTICS

[75] Inventors: Jean-François R. Ancher; Patrick G. Guerret, both of Rueil Malmaison; Michel Langlois, Buc; Jacky A. Tisné-Versailles, Le Pecq, all of France

[73] Assignee: Delalande S.A., Courbevoie, France

[21] Appl. No.: 370,064

[22] Filed: Apr. 20, 1982

[30] Foreign Application Priority Data

Apr. 7, 1982 [FR] France .................................. 82 06094
Apr. 24, 1982 [FR] France .................................. 81 08226

[51] Int. Cl.$^3$ ................... A61K 31/33; A61K 31/495; C07D 243/08; C07D 249/18; C07D 241/04
[52] U.S. Cl. ..................................... 424/244; 544/360; 544/366; 544/370; 544/373; 544/277; 260/244.4; 260/245.5; 260/245.6; 260/245.7; 424/250; 424/251; 546/314; 548/257; 548/325; 548/452

[58] Field of Search ............... 544/360, 366, 370, 373; 424/250, 244; 260/244, 245.5, 245.6, 245.7

[56] References Cited

U.S. PATENT DOCUMENTS

| | | | |
|---|---|---|---|
| 3,331,830 | 7/1967 | Tomcufcik et al. | 544/363 |
| 3,472,854 | 10/1969 | Archer | 544/370 |
| 3,658,822 | 4/1972 | Fauran et al. | 544/370 |
| 3,941,789 | 3/1976 | Renth et al. | 544/370 |
| 4,115,569 | 9/1978 | Weber et al. | 424/250 |
| 4,148,895 | 4/1979 | Lattrell et al. | 424/250 |
| 4,179,505 | 12/1979 | Raeymaekers et al. | 544/370 |

Primary Examiner—Donald G. Daus
Assistant Examiner—S. A. Gibson
Attorney, Agent, or Firm—St. Onge, Steward, Johnston & Reens

[57] ABSTRACT

There are disclosed piperidinio, piperazino and homopiperazino derivatives wherein there is N-substitution by a heterocyclic compound taken from the group benzimidazole, indole, purine or benzotriazole and to the organic or mineral acid addition salts of these derivatives. The process for preparation of such compounds and their use is also disclosed.

9 Claims, No Drawings

PIPERAZINES AND HOMOPIPERAZINES, N-SUBSTITUTED BY AN AROMATIC HETEROCYCLIC GROUP, AND THEIR USE IN THERAPEUTICS

The present invention relates to new piperidinic, piperazinic and homopiperazinic derivatives, N-substituted by a heterocyclic group of the benzimidazole, indole, purine or benzotriazole type, the process for preparing same and the use thereof in therapeutics.

More precisely, the new derivatives of the invention correspond to the formula:

$$Ar-N\underset{(CH_2)_n}{\overset{}{\diagup\!\!\!\diagdown}}X-R \quad (I)$$

in which:
  the pair (X,n) assumes any one of the following values: (N,1), (N,2), (CH,1); R represents:
    a hydrogen atom,
    an alkylcarbonyl or alkyloxycarbonyl group in which the alkyl residue is linear or branched and comprises from 1 to 5 carbon atoms,
    a heterocyclic-carbonyl group (heterocyclic-CO) in which the heterocycle is a furyl, thienyl, tetrahydrofuryl, pyridyl or [(methylthio-2) oxadiazole-1,3,4yl]-5 nucleus,
    a benzoyl, trimethoxy-3,4,5 cinnamoyl, allyloxycarbonyl, (methyl-2 propene-1yl-3) oxycarbonyl, benzyloxycarbonyl or phenoxycarbonyl chain, or
    a phenylthio group, except in the case where X represents the CH group; and
  Ar represents any one of the following nucleii: benzimidazolyl-4(7); (alkyl-2) benzimidazolyl-4(7) in which the alkyl residue comprises from 1 to 4 carbon atoms; (phenyl-2) benzimidazolyl-4(7); (benzyl-2) benzimidazolyl-4(7); purinyl-6, except in the case where the pair (X,R) takes on the value (N,H); benzotriazolyl-4(7); indolyl-7; indolyl-4, but only in the case where the pair (X, n) takes on the value (N, 1).

The invention also relates to the organic or mineral acid addition salts of the derivatives of formula (I).

Among these derivatives in accordance with the invention may be more particularly mentioned those in which the set (X, n, R) assumes the value (N, 1, H) and Ar represents a benzimidazolyl-4(7); benzotriazolyl-4(7); indolyl-4 or indolyl-7 group.

The present invention also relates to the processes for preparing the derivatives of formula (I) and their salts.

Thus:

A/ The compounds of formula (I) in which Ar represents the benzimidazolyl-4(7) nucleus, the pair (X,n) takes on the value (N,1), (N,2) or (CH,1) and R has the same meanings as in formula (I), the pair (X,R) not however being able to take on the values (N,H) and (N, phenylthio), are obtained by a process which consists in a cyclising reduction with hydrogen in the presence of formic acid, preferably in an autoclave at ambient temperature and in the presence of palladium on charcoal (10% of palladium), of the compounds of formula:

$$\underset{NH_2\;NO_2}{\diagdown\!\!\!\diagup}\!\!-N\underset{(CH_2)_n}{\overset{}{\diagup\!\!\!\diagdown}}X-R \quad (II)$$

in which n, X, R have the same meanings as in formula (I), the pair (X, R) not however being able to take on the value (N, H) or (N, phenylthio).

The compounds of formula (II) are obtained by condensation of chloro-3 nitro-2 aniline, preferably in solution in an organic solvent such as DMF, acetonitrile, acetone, an alcohol or toluene for example, in the presence of a basic agent such as potassium carbonate or triethylamine, with the compounds of formula:

$$HN\underset{(CH_2)_n}{\overset{}{\diagup\!\!\!\diagdown}}X-R \quad (III)$$

in which n, X and R have the same meanings as in formula (II).

The compounds of formula (III), as far as they are concerned, are either already known or are prepared in accordance with one of the conventional methods described in the literature.

B/ The compounds of formula (I) for which Ar represents the nucleii: (alkyl-2) benzimidazolyl-4(7) in which the alkyl residue comprises 1 to 4 carbon atoms, (phenyl-2) benzimidazolyl-4(7) or (benzyl-2) benzimidazolyl-4(7), the pair (X, n) takes on the value (N,1), (N,2) or (CH,1) and R has the same meanings as in formula (I), the pair (X, R) not however being able to take on the values (N,H) and (N,phenylthio), are obtained by cyclization of the compounds of formula:

$$\underset{NH_2\;NH_2}{\diagdown\!\!\!\diagup}\!\!-N\underset{(CH_2)_n}{\overset{}{\diagup\!\!\!\diagdown}}X-R \quad (IV)$$

in which n, X and R have the same meanings as in formula (II), preferably in an alcohol solution (ethanol for example), with the hydrochloride of the imidates of formula:

$$R_1-\underset{OEt}{\overset{NH}{\diagup\!\!\!\!\diagdown}} \quad (V)$$

in which $R_1$ represents an alkyl group with 1 to 4 carbon atoms, a phenyl group or a benzyl group.

The compounds of formula (IV) are obtained by hydrogenation, preferably in an alcohol medium and in the presence of palladium on charcoal (10% of palladium), of the compounds of formula (II).

C/ The compounds of formula (I) for which Ar represents the purinyl-6 nucleus, the pair (X, n) takes on the value (N,1), (N,2) or (CH,1) and R has the same meanings as in formula (I), the pair (X,R) not however being able to take on the values (N, H) and (N, phenylthio), are obtained by condensation, preferably in n-butanol, of the compounds of formula (III) with chloro-6 purine.

D/ The compounds of formula (I) for which Ar represents the benzotriazolyl-4(7) nucleus, the pair (X, n) takes on the value (N, 1), (N,2) or (CH,1) and R has the same meanings as in formula (I), the pair (X, R) not however being able to take on the values (N, H) and (N, phenylthio), are obtained by condensation of the compounds of formula (IV) with an alkaline metal nitrite such as sodium nitrite, preferably in aqueous media and in the presence of acetic acid.

E/ The compounds of formula (I) for which Ar represents the indolyl-7 nucleus, the pair (X, n) takes on the value (N, 1), (N, 2) or (CH,1) and R has the same meanings as in formula (I), the pair (X, R) not however being able to take on the values (N, H) and (N, phenylthio), are obtained by cyclizing reduction with hydrogen—preferably in an ethyl acetate medium in the presence of palladium on charcoal (10% of palladium) and in autoclave—of the compounds of formula:

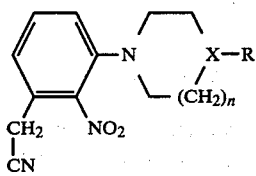

(VI)

in which X, n and R have the same meanings as in formula (III).

The compounds of formula (VI) are obtained by condensation of the compounds of formula (III) with chloro-3 nitro-2 phenylacetonitrile obtained by the action of sodium cyanide, preferably in an alcohol medium, on bromomethyl-1 nitro-2 chloro-3 benzene.

F/ The compound of formula (I) for which Ar represents the indolyl-4 nucleus, the pair (X, n) takes on the value (N, 1) and R represents the hydrogen atom, is obtained by hydrogenolysis—preferably in an ethanol medium and in the presence of palladium on charcoal (5% of palladium)—of the formula (I) compound having the particular structure:

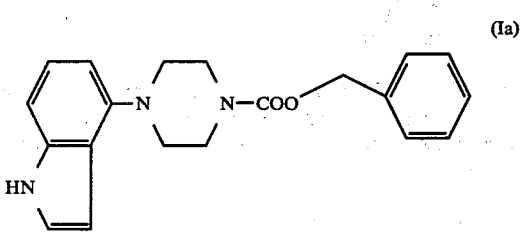

(Ia)

obtained by aromatization with an alkaline metal ferricyanide such as potassium ferricyanide, more especially in an aqueous medium, of indoline of formula:

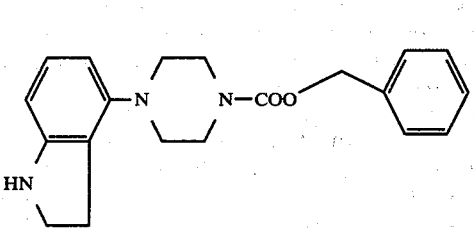

(VII)

This latter is obtained by acid hydrolysis, especially with 1N hydrochloride acid, of the compound of formula:

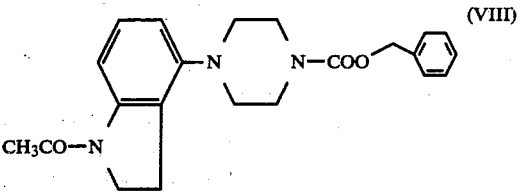

(VIII)

obtained by condensation, in DMF and in the presence of triethylamine, of benzylchloroformiate with the compound of formula:

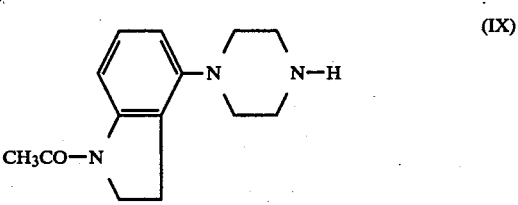

(IX)

itself obtained by condensation, in butoxy-ethanol, in the presence of potassium carbonate and potassium fluoride, of bischloroethylamine hydrochloride with the compound of formula:

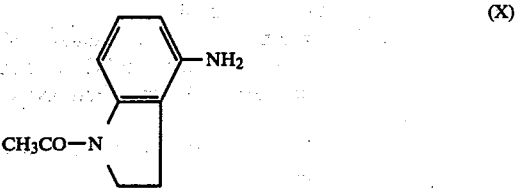

(X)

The compound of formula (X) is obtained by catalytic reduction in the presence of palladium on charcoal (10% of palladium), in an ethanol medium, of the compound of formula:

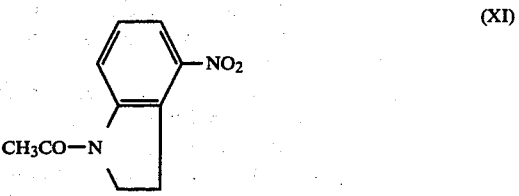

(XI)

which is obtained by acetylation with acetic anhydride of nitro-4 indoline. This latter is prepared by a 3 stage synthesis consisting in treating dinitro-2, 6 toluene with paraformaldehyde in the presence of sodium ethylate, in solution in DMSO, then in treating the (dinitro-2,6) phenyl-2 ethanol thus obtained with sodium sulfide, in the presence of sodium bicarbonate, in solution in water and methanol and finally in cyclizing the (amino-2-nitro-6) phenyl-2 ethanol obtained with 48% hydrobromic acid.

G/ The compounds of formula (I) for which Ar represents the benzimidazolyl-4(7) nucleus, the (alkyl-2) benzimidazolyl-4(7) nucleus in which the alkyl residue comprises 1 to 4 carbon atoms, the (phenyl-2) benzimidazolyl-4(7) nucleus, the (benzyl-2) benzimidazolyl-4(7) nucleus, the purinyl-6 nucleus, the benzotriazolyl-4(7) nucleus or the indolyl-7 nucleus and the set (X, n, R) takes on the value (N, 1, H), or (N, 2, H) are obtained:

either by treating with hydrobromic acid, preferably at 48%, the compounds of formula (I) having the particular structure:

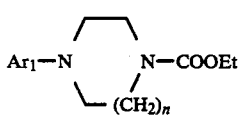
(Ib)

in which n takes on the value 1 or 2 and Ar represents the groups mentioned immediately above, or by treating with aqueous baryte [Ba(OH)$_2$] the compounds of formula (Ib), the compounds of formula (Ib) being prepared in accordance with the processes described under points A/ to E/ above.

H/ The compounds of formula (I) for which the set (X, n, R) takes on the value (N, 1, phenylthio) or (N, 2, phenylthio) are obtained by condensation of N-phenylthiophthalimide with the compounds of formula (I) having the particular structure:

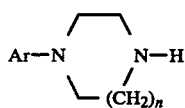
(Ic)

in which n takes the values 1 or 2 and Ar has the same meanings as in formula (I).

The compounds of formula (Ic) are obtained in accordance with the method described in paragraphs G/ and F/ above.

I/ The compounds of formula (I) having the particular structure:

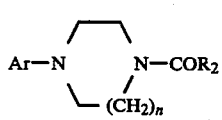
(Id)

in which Ar has the same meanings as in formula (I) and R$_2$ represents an alkyl or alkyloxy group in which the alkyl residue comprises 1 to 5 carbon atoms, a phenyl, furyl, thienyl, pyridyl, tetrahydrofuryl, [(methylthio-2) oxadiazole-1,3,4yl]-5 or trimethoxy-3,4,5 styryl nucleus or an alkyloxy, (methyl-2 propene-1yl-3) oxy, phenoxy or benzyloxy group already obtained in accordance with the methods described in paragraphs A/ to E/ above may also be obtained, depending on the nature of R$_2$, by condensation of the compounds of formula (Ic) with the acid chlorides (or chloroformiates) or the acid anhydrides having respectively the formula:

R$_2$ COCl  (XII) or (R$_2$ CO)$_2$O  (XIIa)

in which R$_2$ has the same meanings as in formula (Id), this condensation being preferably carried out in pyridine or in an aprotic organic solvent such as methylene chloride, DMF or THF and in the presence of triethylamine.

As was pointed out above, the salts of the derivatives of formula (I) may be formed with organic and mineral acids. Among the organic acids there may be more especially mentioned maleic acid and among the mineral acids, hydrobromic acid and hydrochloric acid may be mentioned.

These salts may be prepared by simple reaction of the derivative of formula (I) with the acid, both being possibly in solution in an appropriate solvent such as acetone or ethanol for example.

The following preparations are given by way of example to illustrate the invention.

EXAMPLE 1

(carbethoxy-4 piperazino-1)-4(7) benzimidazole, maleate (I)

Code number: 13

1st step: (carbethoxy-4 piperazino-1)-3 nitro-2 aniline (II)

A suspension of 6.9 g of chloro-3 nitro-2 aniline, 5.7 g of N-carbethoxy-piperazine [(III)] and 5 g of potassium carbonate in 15 ml of DMF is brought to reflux for 15 hours. Then it is poured into iced water, extracted with ethyl acetate, dried on sodium sulfate, filtered, the filtrate is evaporated and the residue crystallized in isopropylic ether. Thus 7 g of the expected compound are isolated.

Yield: 69%

Melting point: 110° C.

By the same process but from the corresponding reagents, the compounds of formula (II) of the invention are obtained which are required for the synthesis of the compounds of formula (I) and more especially the following:

(acetyl-4 piperazino-1)-3 nitro-2 aniline (melting point: 142° C.)

[(methyl-2) propionyl-4 piperazino-1]-3 nitro-2 aniline (melting point: 143° C.)

[(furoyl-2)-4 piperazino-1]-3 nitro-2 aniline (melting point: 155° C.)

[(thienoyl-2)-4 piperazino-1]-3 nitro-2 aniline (melting point: 138° C.)

(benzoyl-4 piperazino-1)-3 nitro-2 aniline (melting point: 190° C.)

[(tetrahydrofuranoyl-2)-4 piperazino-1]-3 nitro-2 aniline (melting point: 156° C.)

(nicotinoyl-4 piperazino-1)-3 nitro-2 aniline (melting point: 188° C.)

(carbethoxy-4 homopiperazino-1)-3 nitro-2 aniline (oil)

(carbethoxy-4 piperidino)-3 nitro-2 aniline (melting point: 77° C.)

2nd step: (carbethoxy-4 piperazino-1)-4 (7) benzimidazole, maleate (I)

A suspension of 7 g of (carbethoxy-4 piperazino-1)-3 nitro-2 aniline (II) obtained in the previous step and 1.4 g of a 50% suspension in water of palladium on charcoal (10% of palladium), in 200 ml of 99% formic acid is left under agitation for two hours, in an autoclave at ambient temperature and under hydrogen pressure. Then 4 ml of 11N hydrochloric acid are added and the whole is brought to reflux for two and a half hours, then it is filtered, the filtrate is evaporated and the residue taken up in water, neutralized with NH$_4$OH, extracted with chloroform, the extract is washed with water, dried on sodium sulfate, filtered, the filtrate is evaporated, the residue is dissolved in acetone and a solution of 2.6 g of maleic acid in 20 ml of acetone is added. The precipitate obtained is filtered and recrystallized in ethanol. 4 g of the expected compound are isolated.

By the same process but from the corresponding reagents, the compounds of formula (I) are obtained shown in Table I below under the code numbers: 2 to 12, 14 to 23 and 30.

EXAMPLE 2 phenyl-2 (carbethoxy-4 piperazino-1)-4(7) benzimidazole (I)

Code number: 28

1st step: (diamino-2,3 Phényl)-4 carbethoxy-1 piperazine (IV)

A suspension of 5 g of (carbethoxy-4 piperazino-1)-3 nitro-2 aniline [(II)] and 0.5 g of palladium on charcoal (10% of palladium) in 100 ml of ethanol is hydrogenated in an autoclave at ambient temperature and at a pressure of 150 millibars for one and a half hour. Then it is filtered, the filtrate evaporated and the residue crystalized in ethyl ether. Thus 2.8 g of the desired compound are isolated.

Yield: 63%

Melting point: 107° C.

By the same process but from the corresponding reagents the compounds of formula (IV) are obtained which are required for the synthesis of the compound of formula (I).

2nd step: phenyl-2(carbethoxy-4 piperazino-1)-4 (7) benzimidazole (I)

A solution of 2.7 g of (diamino-2,3 phenyl)-4 carbethoxy-1 piperazine obtained in the preceding step and 2.2 g of phenylimidate hydrochloride [(V), $R_1=C_6H_5$] in 30 ml of ethanol is brought to reflux for 30 minutes. Then the solvent is evaporated, the residue is taken up in water, extracted with ethyl acetate, the extracte is washed with water, dried on sodium sulfate, filtered, the filtrate is evaporated and the residue crystallized in an ethyl acetate and isopropylic ether mixture. Thus 2.6 g of the expected compound are isolated.

By the same process, but from the corresponding reagents, the compounds of formula (I) are obtained which are shown in Table I below under code numbers: 26 and 27.

EXAMPLE 3

(carbethoxy-4 piperazino-1)-6 purine (I)

Code number: 25

A solution of 1.5 g of chloro-6 purine and 3.3 g of N-carbethoxypiperazine [(III)] in 15 ml of butanol is brought to 60° C. for 30 minutes. Then the reaction mixture is filtered, the filtered precipitate is rinsed with ethyl ether, then washed with water and recrystallized in ethanol. Thus, 2 g of the expected compound are obtained.

EXAMPLE 4

(ethoxycarbonyl-4 piperazino-1)-4 (7) benzotriazole (I)

Code number: 38

To a mixture of 17 ml of acetic acid and 35 ml of water are added 7.5 g of (diamino-2,3 phenyl)-4 carbethoxy-1 piperazine [(IV) obtained in the first step of example 2], then the solution is cooled to 0° C. to which is then added a solution of 2.3 g of sodium nitrite in 7.6 ml of water and it is left to return to room temperature. After 2 hours at room temperature, the reaction medium is neutralized with NH₄OH and filtered. The filtrate is saturated with sodium chloride, then extracted with chloroform. The product obtained by filtration is added to the chloroform phase, the chloroform phase obtained is dried on sodium sulfate, filtered and the filtrate evaporated. The residue is chromatographed on a silica column (medium pressure liquid chromatography), elution being carried out with ethyl acetate. The product resulting from this chromatography is then recrystallized in an isopropyl ether (50%)—isopropyl alcohol (50%) mixture; 5.6 g of the expected product are thus isolated.

EXAMPLE 5

(carbethoxy-4piperazino-1)-7 indole (I)

Code number: 29

1st step: chloro-3 nitro-2 phenylacetonitrile

A solution of 2.2 g of bromomethyl-1 nitro-2 chloro-3 benzene and 0.5 g of sodium cyanide in 40 ml of absolute alcohol is left under agitation for 24 hours at room temperature. Then it is filtered, the filtrate evaporated, the residue is taken up in methylene chloride, the obtained solution is dried on sodium sulfate, filtered, the filtrate is evaporated and the residue chromatographed on a silica column [eluent: n-heptane (75%)—ethyl acetate (25%)]. Thus 1 g of the expected compound is obtained:

Yield: 60%

Melting point: 62° C.

Empirical formula: $C_7H_5ClN_2O_2$

Molecular weight: 184.58

2nd step: (carbethoxy-4 piperazino-1)-3 nitro-2 phenylacetonitrile (VI)

A mixture of 3 g of chloro-3 nitro-2 phenylacetonitrile obtained in the preceding step and 50 ml of N-carbethoxy piperazine [(III)] is brought to 130° C. for 4 hours. Then it is thrown on ice, extracted with ethyl acetate, the mixture obtained is dried on sodium sulfate, filtered, the filtrate is evaporated and the residue is chromatographed on a silica column [eluent: n-heptane (70%)—ethyl acetate (30%) ]. Thus, 2.6 g of the expected product are obtained.

Yield: 50%

Melting point: 85° C.

Empirical formula: $C_{15}H_{18}N_4O_4$

Molecular weight: 318.33

3rd step: (carbethoxy-4 piperazino-1)-7 indole (I)

A suspension of 1.9 g of formula (VI) compound, obtained in the preceding step, and 0.9 g of palladium on charcoal (10% of palladium) in 60 ml of ethyl acetate is hydrogenated in an autoclave at a pressure of 20 kg and at 80° C. for 3 hours. Then the reaction mixture is filtered, the filtrate is evaporated and the residue chromatographed on a silica column [eluent: n-heptane (60%)—ethyl acetate (40%)]. Thus 1 g of the expected compound is obtained.

EXAMPLE 6

Piperazino-4 indole (I)

Code number: 41

A suspension of 5.7 g of (benzyloxycarbonyl-4 piperazino-1)-4 indole [(Ia) code No. 40] and 0.6 g of palladium on charcoal (5% of palladium) in 100 ml of ethanol is hydrogenated under pressure at room temperature. Then the reaction mixture is filtered, the filtrate evaporated and the residue is chromatographed on a silica column (medium pressure liquid chromatography) [elution by the mixture: CH2Cl2(90%)—methanol (9%)—NH4OH (1%)]. The resulting product is then sublimated (sublimation point=160° C. under 0.05 mm of Hg). Thus 2 g of the expected product are isolated.

EXAMPLE 7

(benzyloxycarbonyl-4 piperazino-1)-4 indole (Ia)

Code number: 40

To a solution, brought to reflux, of 9.5 g of potassium ferricyanide in 200 ml of water are added 9.5 g of (benzyloxycarbonyl-4 piperazino-1)-4 indoline (VII). Then it is left at reflux for 2 hours and a further portion of 9.5 g of potassium ferricyanide in 100 ml of water is added. The reaction mixture is left at reflux for three hours, then filtered and extracted with ethyl acetate. The organic phases are evaporated and the residue is chromatographed on a silica column (medium pressure liquid chromatography), the eluent being formed by a 40% ethyl acetate -60% n-heptane mixture. Thus 5.7 g of the expected product are isolated.

EXAMPLE 8

(benzyloxycarbonyl-4 piperazino-1)-4 indoline (VII)

A solution of 12.5 g of acetyl-1 (benzyloxy-carbonyl-4 piperazino-1)-4 indoline (VIII) in 400 ml of 1N hydrochloric acid is heated to 80° C. for 3 hours. After cooling, the reaction mixture is neutralized with NH4OH, extracted with ethyl acetate, the organic phase is evaporated and the residue chromatographed on a silica column (medium pressure liquid chromatography), elution being carried out with the ethyl acetate/heptane (60/40) mixture. Thus 9.4 g (yield=81%) of the expected product are obtained.

NMR spectrum δppm (CDCl3)=7.35, s and 5.2, s (7 H: COOCH2C6H5) 7.0, m and 6.25, m (3 aromatic H) 3.55, m and 2.9, m (12 H:

and —CH2—CH2—)

EXAMPLE 9

Acetyl-1 (benzyloxycarbonyl-4 piperazino-1)-4 indoline (VIII)

To a solution, cooled to 0° C., of 13 g of acetyl-1 piperazino-4 indoline (IX) in 450 ml of DMF are added 23 ml of triethylamine, then 11 ml of benzyl chloroformiate. The reaction mixture is agitated at room temperature for 20 minutes, then the solvent is evaporated and the residue taken up in a mixture of water and ethyl acetate, decanted, the organic phase is dried on sodium sulfate, filtered and the filtrate evaporated. The residue is chromatographed on a silica column (medium pressure liquid chromatography), elution being carried out with the ethyl acetate/heptane (50/50) mixture. Thus, 13 g (yield=70%) of the expected product are obtained.

Melting point: 150° C.
Empirical formula: C22H25N2O3
Molecular weight: 365.44

EXAMPLE 10

Acetyl-1 piperazino-4 indoline (IX)

To a solution, brought to reflux, of 15.1 g of bis-chloroethylamine hydrochloride in 400 ml of butoxyethanol are added 11.8 g of potassium carbonate, then 5 g of potassium fluoride, then 14.8 g of amino-4 acetyl-1 indoline (X). The reaction mixture is left at reflux for 9 hours, then the solvent is evaporated and the residue chromatographed on a silica column (medium pressure liquid chromatography), elution being carried out with a 93% chloroform—6.5% methanol-0.5% NH4OH mixture. Thus 4.3 g (yield=21%) of the expected product are isolated.

Melting point: 160° C.
Empirical formula: C14H19N3O
Molecular weight: 245.32

EXAMPLE 11

Acetyl-1 amino-4 indoline (X)

A suspension of 20 g of acetyl-1 nitro-4 indoline (XI) and 4 g of palladium on charcoal (10% of palladium) in 600 ml of ethanol is hydrogenated under a hydrogen pressure of 40 kg at a temperature of 80° C. Then the reaction mixture is filtered and the filtrate evaporated. A crystallized product is obtained which corresponds to the expected product.

Melting point: 178° C.
Yield: ~100%
Empirical formula: C10H12N2O
Molecular weight: 176.21

EXAMPLE 12

Acetyl-1 nitro-4 indoline (XI)

35 g of nitro-4 indoline are dissolved in 100 ml of acetic acid anhydride then, the obtained mixture is diluted with isopropylic ether and the precipitate obtained is filtered which corresponds to the expected compound.

Melting point: 143° C.
Yield: ~100%
Empirical formula: C10H10N2O3
Molecular weight: 206.20

EXAMPLE 13 nitro-4 indoline

A mixture of 42 g of (amino-2 nitro-6) phenyl-2 ethanol in 500 ml of 48% hydrobromic acid is brought to reflux for 15 hours. Then the reaction mixture is diluted with 2 liters of water and filtered, the aqueous phase is neutralized with NH4OH, extracted with ethyl acetate, the extract is dried on sodium sulfate, filtered and the filtrate is evaporated. The residue is chromatographed on a silica column (medium pressure liquid chromatography), elution being carried out with the 85/15 ethyl acetate/heptane mixture. Thus 8.2 g of bromo-7 nitro-4 indoline are obtained (melting point=112° C.), then 14.2 g of nitro-4 indoline (melting point=105° C).

It should be noted here that bromo-7 nitro-4 indoline acetylated as in example 12 then hydrogenated as in example 11 also leads to acetyl-1 amino-4 indoline (X).

EXAMPLE 14

(amino-2 nitro-6) phenyl-2 ethanol

A solution of 53 g of (dinitro-2,6) phenyl-2 ethanol in 600 ml of methanol is heated to 55°–60° C., to which is then added a solution of 216 g of sodium sulfide and 67.2 g of sodium bicarbonate in 750 ml of water. The obtained reaction mixture is left for 1 hour at 60° C. then diluted with 2 liters of water, extracted with ethyl acetate, the extract is dried on sodium sulfate, filtered and the filtrate evaporated. Thus 42.1 g (yield=92%) of the expected product (crystallized) are obtained.

Melting point: 92° C.
Empirical formula: $C_8H_{10}N_2O_3$
Molecular weight: 182.18

EXAMPLE 15

(dinitro-2,6) phenyl-2 ethanol

To a solution of 76 g of dinitro-2,6 toluene in 400 ml of DMSO are added 12.6 g of paraformaldehyde, then 28.5 g of sodium ethylate. The solution is left under agitation at room temperature for 96 hours, then the reaction medium is poured on 2 kg of ice, neutralized with hydrochloric acid, filtered, the aqueous phase is extracted with ethyl acetate and the precipitate obtained during filtration is added to the organic phase. The organic phase obtained is dried on sodium sulfate and the filtrate is evaporated. The residue is chromatographed on a silica column [medium pressure liquid chromatography—eluent: (90/10)heptane-ethyl acetate mixture]. Thus, 77 g of the expected product are obtained.

Yield: 87%
Melting point: 68° C.
Empirical formula: $C_7H_8N_2O_5$
Molecular weight: 212.16

EXAMPLE 16

(piperazino-1)-4(7) benzimidazole, tribromhydrate (I)

Code number: 1

A solution of 1.5 g of the formula (I) compound, code No. 13, prepared in example 1, in 60 ml of 48% hydrobromic acid is heated at 110° C. for 3 hours. Then the solvent is evaporated in a vacuum, the residue is crystallized in ethanol and filtered. 2 g of the expected compound are isolated.

By the same process, but from the corresponding reagents, the compounds of formula (I) were obtained, shown under code numbers 32 to 37, 39 and 42 in Table I below.

EXAMPLE 17

(piperazino-4 (7) benzotriazole, dihydrochloride (I)

Code number: 39

A solution of 3.6 g of (ethoxycarbonyl-4 piperazino-1)-4 (7) benzotriazole [(I), code No. 38] in 200 ml of 0.5N $Ba(OH)_2$ is brought to reflux for 2 hours. Then a further 200 ml of 0.5N $Ba(OH)_2$ is added, the reaction medium is left for 2 hours and again 50 ml of 0.5N $Ba(OH)_2$ are added and left for 3 hours at reflux. After cooling, the reaction mixture is neutralized by bubbling carbonic gas through said reaction mixture, then it is filtered, the filtrate is evaporated, the filtration precipitate and the residue are dissolved in chloroform, the chloroform phase is dried on sodium sulfate, filtered and the filtrate evaporated. This residue is chromatographed on a silica column [medium pressure liquid chromatography—eluent: 80% methyl chloride—19% methanol—1% $NH_4OH$ mixture]. The product thus isolated is then crystallized in the minimum of ethanol. Thus, 1.55 g of product is obtained which is dissolved in 50 ml of warm ethanol. 4 ml of 8N hydrochloric ethanol are added and the precipitate obtained is filtered. Thus, 1.21 g of expected product are obtained.

By the same process, but from the corresponding reagents, compounds (I) are obtained, shown under code numbers 1, 32 to 37 and 42 in Table I.

EXAMPLE 18

(phenylthio-4 piperazino-1)-4 (7) benzimidazole (I)

Code number: 24

A suspension of 6.1 g of formula (I) compound, code No. 1 and prepared in example 16, of 8.4 g of N-phenylthiophthalimide in 300 ml of benzene and 30 ml of ethanol is heated to reflux for 4 hours, then it is cooled to 10° C., filtered, the filtrate is evaporated, and the residue taken up in ethylacetate, the organic phase obtained is filtered, the filtrate is evaporated and the residue chromatographed on a silica column (eluent: ethyl acetate). 2.9 g of the expected product are obtained after crystallization in ethyl ether.

EXAMPLE 19

(n-pentanoyl-4 piperazino-1)-4 (7) benzimidazole (I)

Code number: 5

To a solution, cooled to 0° C., of 5.2 g of the compound of formula (I), code No. 1, prepared in example 16, in 100 ml of DMF are added over 10 minutes, 9.5 ml of triethylamine and the reagents are left in contact for 30 minutes, then 1.9 ml of n-pentanoic acid chloride are added over 15 minutes and the reagents are left in contact for one and a half hour, then the reaction mixture is poured into iced water, the mixture obtained is extracted with chloroform, the chloroform phase is dried on sodium sulfate, filtered, the filtrate is evaporated and the residue is crystallized in a 50/50 isopropyl ether-isopropyl alcohol mixture. Thus, 1.1 g of the expected compound is isolated.

By the same process, but from the corresponding reagents, the compounds of formula (I) are obtained, shown in Table I below under code numbers 2 to 4, 6 to 23, 38 and 40.

TABLE I $$Ar-N\underset{(CH_2)_n}{\overset{X-R}{\diagup}} \quad (I)$$

| Code Number | Ar— | —N(CH₂)ₙ(X—R) | Form | Empirical formula | Molecular weight | Melting point (°C.) | Yield (%) | ELEMENTARY ANALYSIS % | C | H | N |
|---|---|---|---|---|---|---|---|---|---|---|---|
| 1 | 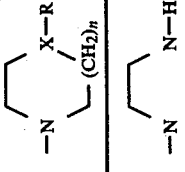 substitution in 4(7) | 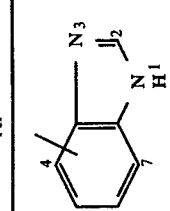 N—H | tribrom-hydrate | C₁₁H₁₇Br₃N₄ | 445.01 | >260 | 83 | Cal.<br>Obt. | 29.69<br>29.78 | 3.25<br>3.89 | 12.59<br>12.69 |
| 2 | " | 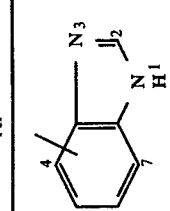 NCOCH₃ | base | C₁₃H₁₆N₄O | 244.29 | 173 | 30 | Cal.<br>Obt. | 63.91<br>63.92 | 6.60<br>6.60 | 22.94<br>22.84 |
| 3 | " | 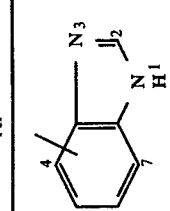 N—CO—CH(CH₃)₂ | base | C₁₅H₂₀N₄O | 272.34 | 154 | 45 | Cal.<br>Obt. | 66.15<br>66.18 | 7.40<br>7.66 | 20.57<br>20.36 |
| 4 | " | 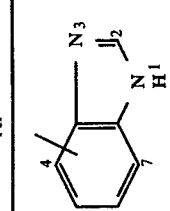 N—CO—C(CH₃)₃ | base | C₁₆H₂₂N₄O | 286.37 | 214 | 42 | Cal.<br>Obt. | 67.10<br>66.86 | 7.74<br>8.07 | 19.57<br>19.37 |
| 5 | " | 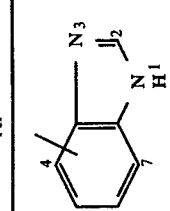 N—COC₄H₉ᵣ | base | C₁₆H₂₂N₄O | 286.37 | 107 | 23 | Cal.<br>Obt. | 67.10<br>66.96 | 7.74<br>8.04 | 19.57<br>19.52 |
| 6 | " | 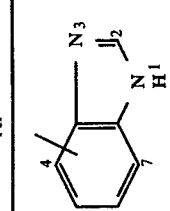 N—CO-furyl | base | C₁₆H₁₆N₄O₂ | 296.32 | 200 | 61 | Cal.<br>Obt. | 64.85<br>64.68 | 5.44<br>5.44 | 18.91<br>19.20 |

TABLE I-continued $$Ar-N\underset{(CH_2)_n}{\overset{X-R}{\diagdown}} \quad (I)$$

| Code Number | Ar— | [structure] | Form | Empirical formula | Molecular weight | Melting point (°C.) | Yield (%) | Elementary Analysis % | | C | H | N |
|---|---|---|---|---|---|---|---|---|---|---|---|---|
| 7 | " | thiophene-N-CO-piperazine | base | C₁₆H₁₆N₄OS | 312.39 | 199 | 36 | Cal. | | 61.51 | 5.16 | 17.94 |
| | | | | | | | | Obt. | | 61.48 | 5.24 | 18.14 |
| 8 | " | phenyl-N-CO-piperazine | base | C₁₈H₁₈N₄O | 306.36 | 230 | 52 | Cal. | | 70.56 | 5.92 | 18.29 |
| | | | | | | | | Obt. | | 70.42 | 6.10 | 18.28 |
| 9 | " | tetrahydrofuran-N-CO-piperazine | base | C₁₆H₂₀N₄O₂ | 300.35 | 220 | 35 | Cal. | | 63.98 | 6.71 | 18.66 |
| | | | | | | | | Obt. | | 63.76 | 6.76 | 18.87 |
| 10 | " | pyridyl-N-CO-piperazine | base | C₁₇H₁₇N₅O | 307.35 | 204 | 46 | Cal. | | 66.43 | 5.58 | 22.79 |
| | | | | | | | | Obt. | | 66.41 | 5.49 | 22.51 |
| 11 | " | 3,4,5-trimethoxycinnamoyl-piperazine | base | C₂₃H₂₆N₄O₄ | 422.47 | 219 | 50 | Cal. | | 65.30 | 6.20 | 13.26 |
| | | | | | | | | Obt. | | 65.66 | 6.28 | 13.15 |
| 12 | " | oxadiazole-SCH₃-N-CO-piperazine | base | C₁₅H₁₆N₆O₂S | 344.39 | 170 | 45 | Cal. | | 52.31 | 4.68 | 24.40 |
| | | | | | | | | Obt. | | 52.06 | 4.65 | 24.34 |

TABLE I-continued $$Ar-N\underset{(CH_2)_n}{\overset{X-R}{\diagup}} \quad (I)$$

| Code Number | Ar— | $-N\underset{(CH_2)_n}{\overset{X-R}{\diagup}}$ | Form | Empirical formula | Molecular weight | Melting point (°C.) | Yield (%) | ELEMENTARY ANALYSIS % | | C | H | N |
|---|---|---|---|---|---|---|---|---|---|---|---|---|
| 13 | imidazole (substitution in 4(7)) | N—COOEt piperazine | maleate | $C_{18}H_{22}N_4O_6$ | 390.39 | 173 | 45 | Cal. Obt. | | 55.38 55.47 | 5.68 5.80 | 14.35 14.25 |
| 14 | " | N—COOEt homopiperazine | maleate | $C_{19}H_{24}N_4O_6$ | 404.41 | 157 | 70 | Cal. Obt. | | 56.42 56.57 | 5.98 6.05 | 13.86 13.85 |
| 15 | " | N—COOCH$_3$ piperazine | base | $C_{13}H_{16}N_4O_2$ | 260.29 | 144 | 56 | Cal. Obt. | | 59.98 59.83 | 6.20 6.10 | 21.53 21.43 |
| 16 | " | N—COO—CH$_2$CH=CH$_2$ piperazine | base | $C_{15}H_{18}N_4O_2$ | 286.33 | 160 | 71 | Cal. Obt. | | 62.92 62.84 | 6.34 6.24 | 19.57 19.44 |
| 17 | " | N—COO—CH$_2$C(CH$_3$)=CH$_2$ piperazine | base | $C_{16}H_{20}N_4O_2$ | 300.25 | 142 | 77 | Cal. Obt. | | 63.98 63.78 | 6.71 6.82 | 18.66 18.92 |
| 18 | " | N—COO—CH(CH$_3$)$_2$ piperazine | base | $C_{15}H_{20}N_4O_2$ | 288.34 | 159 | 67 | Cal. Obt. | | 62.48 62.40 | 6.99 7.12 | 19.43 19.64 |

TABLE I-continued $$Ar-N\begin{pmatrix}X-R\\(CH_2)_n\end{pmatrix} \quad (I)$$

| Code Number | Ar— | $-N\begin{pmatrix}X-R\\(CH_2)_n\end{pmatrix}$ | Form | Empirical formula | Molecular weight | Melting point (°C.) | Yield (%) | ELEMENTARY ANALYSIS % | C | H | N |
|---|---|---|---|---|---|---|---|---|---|---|---|
| 19 | " |  N—COOC₄H₉ᵗ | base | C₁₆H₂₂N₄O₂ | 302.37 | 110 | 68 | Cal. Obt. | 63.55 63.63 | 7.33 7.13 | 18.53 18.76 |
| 20 | " | 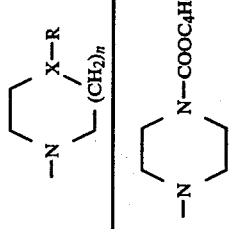 N—COO—C(CH₃)₃ | base | C₁₆H₂₂N₄O₂ | 302.37 | 209 | 65 | Cal. Obt. | 63.55 63.75 | 7.33 7.32 | 18.53 18.70 |
| 21 | " |  N—COO—CH₂CH₂CH(CH₃)₂ | base | C₁₆H₂₂N₄O₂ | 302.37 | 160 | 45 | Cal. Obt. | 63.55 63.49 | 7.33 7.51 | 18.53 18.34 |
| 22 | " |  N—COO—CH₂—φ | base | C₁₉H₂₀N₄O₂ | 336.38 | 153 | 51 | Cal. Obt. | 67.84 67.58 | 5.99 5.91 | 16.66 16.92 |
| 23 | " |  N—COO—φ | base | C₁₈H₁₈N₄O₂ | 322.36 | 197 | 64 | Cal. Obt. | 67.06 66.85 | 5.63 5.70 | 17.38 17.46 |
| 24 | " |  N—S—φ | base | C₁₇H₁₈N₄S | 310.41 | 145 | 31 | Cal. Obt. | 65.77 65.66 | 5.85 5.73 | 18.05 17.74 |

TABLE I-continued
(I)
| Code Number | Ar— | Form | Empirical formula | Molecular weight | Melting point (°C.) | Yield (%) | | ELEMENTARY ANALYSIS % | | |
|---|---|---|---|---|---|---|---|---|---|---|
| | | | | | | | | C | H | N |
| 25 | 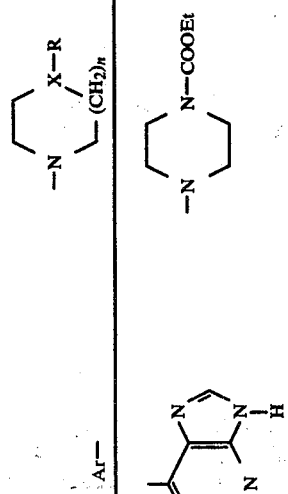 | base | $C_{12}H_{16}N_6O_2$ | 276.30 | >260 | 71 | Cal. Obt. | 52.16 51.99 | 5.84 5.77 | 30.42 30.56 |
| 26 | 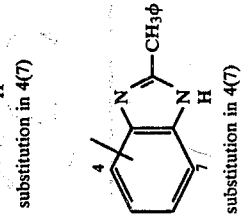 substitution in 4(7) | chlorhydrate | $C_{15}H_{21}ClN_4O_2$ | 324.81 | 202 | 55 | Cal. Obt. | 55.46 55.16 | 6.52 6.39 | 17.25 17.43 |
| 27 | 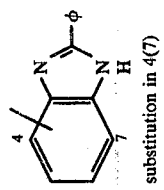 substitution in 4(7) | base | $C_{21}H_{24}N_4O_2$ | 364.43 | 158 | 55 | Cal. Obt. | 69.21 69.26 | 6.64 ~6.85 | 15.3 15.64 |
| 28 | substitution in 4(7) | base | $C_{20}H_{22}N_4O_2$ | 350.41 | 171 | 73 | Cal. Obt. | 68.55 68.76 | 6.33 6.46 | 15.99 16.02 |

TABLE I-continued
(I)
| Code Number | Ar— | | Form | Empirical formula | Molecular weight | Melting point (°C.) | Yield (%) | ELEMENTARY ANALYSIS % | | C | H | N |
|---|---|---|---|---|---|---|---|---|---|---|---|---|
| 29 | 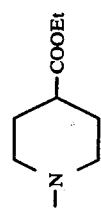 | | base | C$_{15}$H$_{19}$N$_3$O$_2$ | 273.23 | 154 | 60 | Cal. Obt. | | 65.93 65.95 | 7.01 7.13 | 15.38 15.08 |
| 30 | 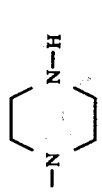 Substitution in 4(7) |  | base | C$_{15}$H$_{19}$N$_3$O$_2$ | 273.23 | 168 | 47 | Cal. Obt. | | 65.93 65.78 | 7.01 7.06 | 15.38 15.47 |
| 32 | 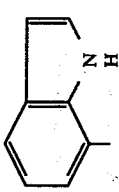 Substitution in 4(7) | 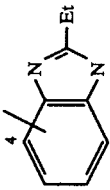 | hydrated base | C$_{12}$H$_{16}$N$_4$ + 0.7% H$_2$O | 217.81 | 206 | 32 | Cal. Obt. | | 66.17 66.09 | 7.49 7.65 | 25.72 25.29 |
| 33 | 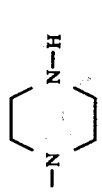 Substitution in 4(7) | ″ | base | C$_{13}$H$_{18}$N$_4$ | 230.31 | 212 | 43 | Cal. Obt. | | 67.79 67.50 | 7.88 8.18 | 24.33 24.06 |

TABLE I-continued

(I)

| Code Number | Ar— | | Form | Empirical formula | Molecular weight | Melting point (°C.) | Yield (%) | ELEMENTARY ANALYSIS % | | | |
|---|---|---|---|---|---|---|---|---|---|---|---|
| | | | | | | | | | C | H | N |
| 34 | 2-isopropyl-benzimidazole, Substitution in 4(7) | piperazine | base | $C_{14}H_{20}N_4$ | 244.33 | 226 | 70 | Cal. Obt. | 68.82 68.67 | 8.25 8.39 | 22.93 22.63 |
| 35 | 2-n-butyl-benzimidazole, Substitution in 4(7) | | base | $C_{15}H_{22}N_4$ + 0.7% $H_2O$ | 260.18 | 148 | 48 | Cal. Obt. | 69.24 69.06 | 8.60 8.48 | 21.54 21.43 |
| 36 | benzimidazole, Substitution in 4(7) | piperazine | base | $C_{12}H_{16}N_4$ | 216.80 | 190 | 45 | Cal. Obt. | 66.48 66.75 | 7.44 7.26 | 25.85 26.05 |
| 37 | 2-phenyl-benzimidazole, substitution in 4(7) | piperazine | hydrated dichlorhydrated | $C_{17}H_{20}Cl_2N_4$ + 0.7% $H_2O$ | 353.72 | >266 | 53 | Cal. Obt. | 57.72 57.23 | 5.78 5.86 | 15.84 15.18 |

TABLE I-continued $$Ar-N\diagup\diagdown X-R \atop \diagdown\diagup (CH_2)_n \qquad (I)$$

| Code Number | Ar— | —N(X-R)(CH₂)ₙ | Form | Empirical formula | Molecular weight | Melting point (°C.) | Yield (%) | ELEMENTARY ANALYSIS % | | C | H | N |
|---|---|---|---|---|---|---|---|---|---|---|---|---|
| 38 |  substitution in 4(7) | 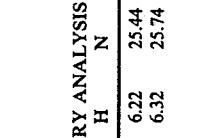 N—COOEt | base | C₁₃H₁₇N₅O₂ | 275.31 | 158 | 73 | Cal. Obt. | | 56.71 56.80 | 6.22 6.32 | 25.44 25.74 |
| 39 | " | 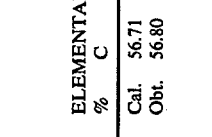 N—H | diHCl | C₁₀H₁₅Cl₂N₅ | 276.17 | 196 | 57 | Cal. Obt. | | 43.49 43.77 | 5.47 5.45 | 25.36 25.62 |
| 40 | 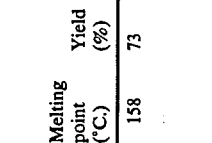 | 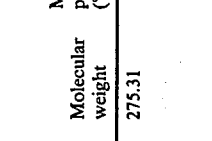 N—COO—CH₂—φ | base | C₂₀H₂₁N₃O₂ | 335.38 | 135 | 62 | NMR: δ ppm (CDCl₃) = 8.2, m (NH); 7.35, s, 7.1, m and 6.5, m (10 aromatic H); 5.2, s (CH₂—φ); 3.7 and  3.2, m (N | | | | |
| 41 | " | 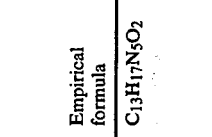 NH | base | C₁₂H₁₅N₃ | 201.26 | 208 | 58 | Cal. Obt. | | 71.61 71.45 | 7.51 7.56 | 20.88 20.70 |
| 42 | 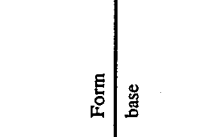 | " | base | C₁₂H₁₅N₃ | 201.26 | 174 | 29 | Cal. Obt. | | 71.61 71.49 | 7.51 7.71 | 20.88 20.89 |

The derivatives of formula (I) and their acid addition salts were tested on laboratory animals and showed pharmacological activities, in particular in the cardiovascular field, more especially as antihypertensive agents.

The antihypertensive activity was revealed by oral administration of the compounds of the invention to S.H.R. rats (genetically hypertensive). The arterial blood pressure was recorded on an APELAB-BP recorder 8002-and an electromechanical counter provided a direct reading of the heartbeat rate. The measurements were taken at 0 hour, 2 hours, 4 hours, 6 hours and 24 hours after administration of the compounds tested.

Acute toxicity was assessed intravenously in mice according to the method of MILLER and TAINTER described in Proc. Soc. Exp. Biol. Med. 57, 261 (1944).

To illustrate the invention, the results obtained with some of the compounds of the invention are shown in Table II below in which the symbols AHY, ΔPA and ΔFC have the following meanings:

AHY = % of rats whose arterial blood pressure drops by a value greater than or equal to 20% of the initial value or is brought down to a value less than 150 mmHg, ΔPA = % variation of the arterial blood pressure in all the animals tested with respect to the initial blood pressure, ΔFC = % variation of the heart-beat rate of all the animals tested with respect to the initial rate.

TABLE II

| Code No. of the tested compounds of the invention | Acute toxicity (mice) LD 50 in mg/kg/i.v. | Antihypertensive activity (S.H.R. rats) | | | |
|---|---|---|---|---|---|
| | | Dose | Time | AHY | ΔPA | ΔFC |
| 1 | 125 | 50 | 4 | 100 | −20 | 0 |
| | | | 6 | 71 | −19 | 0 |
| | | | 24 | 28 | −9 | −7 |
| 3 | at 200 (0%) | 50 | 2 | 28 | −15 | −5 |
| | | | 4 | 14 | −8 | −5 |
| | | | 6 | 57 | −14 | +1 |
| | | | 24 | 43 | −9 | −4 |
| 7 | at 200 (0%) | 50 | 2 | 100 | −31 | −5 |
| | | | 4 | 86 | −23 | −11 |
| | | | 6 | 86 | −23 | −8 |
| | | | 24 | 0 | −2 | −9 |
| 12 | 0% at 1000 (p.o.) | 50 | 2 | 100 | −43 | −12 |
| | | | 4 | 100 | −38 | −13 |
| | | | 6 | 86 | −30 | −6 |
| | | | 24 | 43 | −18 | −13 |
| 13 | 160 | 50 | 2 | 100 | −40 | +2 |
| | | | 4 | 100 | −35 | 0 |
| | | | 6 | 86 | −34 | 0 |
| | | | 24 | 28 | −14 | −5 |
| 17 | at 200 (0%) | 50 | 2 | 100 | −26 | +8 |
| | | | 4 | 33 | −15 | +8 |
| | | | 6 | 67 | −21 | +3 |
| | | | 24 | 33 | −11 | 0 |
| 21 | 195 | 50 | 2 | 86 | −27 | −7 |
| | | | 4 | 71 | −23 | +3 |
| | | | 6 | 100 | −25 | +1 |
| | | | 24 | 14 | −6 | −6 |
| 24 | 0% at 1000 (p.o.) | 50 | 2 | 71 | −21 | +2 |
| | | | 4 | 100 | −23 | 0 |
| | | | 6 | 57 | −19 | 0 |
| | | | 24 | 14 | 0 | −3 |
| 25 | at 200 (0%) | 50 | 2 | 57 | −21 | +2 |
| | | | 4 | 42 | −22 | +7 |
| | | | 6 | 71 | −20 | +2 |
| | | | 24 | 0 | −3 | +15 |
| 26 | 200 | 50 | 2 | 100 | −30 | −9 |
| | | | 4 | 100 | −26 | −5 |
| | | | 6 | 86 | −22 | −2 |
| | | | 24 | 14 | −8 | +2 |
| 30 | 185 | 50 | 2 | 42 | −15 | −2 |
| | | | 4 | 28 | −18 | −3 |
| | | | 6 | 70 | −23 | −2 |
| | | | 24 | 56 | −21 | −4 |
| 39 | 96 | 25 | 4 | 80 | −26 | −7 |
| | | | 6 | 100 | −34 | −5 |
| | | | 24 | 40 | −17 | +5 |
| 41 | 35 | 10 | 2 | 86 | −38 | 0 |
| | | | 4 | 100 | −46 | −8 |
| | | | 6 | 86 | −27 | −2 |
| | | | 24 | 28 | −19 | −2 |
| 42 | 70 | 10 | 2 | 33 | −15 | −10 |
| | | | 4 | 50 | −25 | −10 |
| | | | 6 | 100 | −29 | −22 |
| | | | 24 | 17 | −19 | +7 |

As Table II shows, the compounds of the invention, showing little toxicity, present a sufficiently interesting antihypertensive activity for use in therapeutics.

The present application also relates to the use, as medicaments, of the derivatives of formula (I) and their pharmaceutically acceptable acid addition salts, more especially for the treatment of troubles of the cardiovascular system and in particular as antihypertensive medicaments.

The invention finally relates to pharmaceutical compositions containing, as active ingredient(s), at least one of the above-defined medicaments in association with a pharmaceutically acceptable medium. These compositions will be normally administered orally in the form of tablets, pills, capsules taken in one or several doses up to a total of 500 mg/day of active principle.

We claim:

1. Novel piperazines and homopiperazines corresponding to the formula:

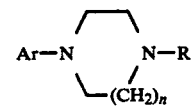

in which:
n = 1 or 2;
R represents:
 a hydrogen atom,
 an alkylcarbonyl or alkyloxycarbonyl group where the alkyl residue is linear or branched and comprises 1 to 5 carbon atoms,
 a heterocyclic—carbonyl group (heterocyclic—CO) in which the heterocycle is a furyl, thienyl, tetrahydrofuryl, pyridyl or [(methylthio-2) oxadiazole-1,3,4, yl]-5 nucleus,
 a benzoyl, trimethoxy-3,4,5 cinnamoyl, allyloxycarbonyl, (methyl-2 propene-1 yl-3) oxycarbonyl, benzyloxycarbonyl or phenoxycarbonyl chain, or
 a phenylthio group, and
Ar represents any one of the following nucleii: benzimidazolyl 4(7); (alkyl-2) benzimidazolyl-4(7) in which the alkyl residue comprises 1 to 4 carbon atoms; (phenyl-2) benzimidazolyl-4(7) ; (benzyl-2)

benzimidazolyl-4(7); benzotriazolyl-4(7); indolyl-7; indolyl-4, but only in the case there n=1; and the acid addition salts thereof.

2. The piperazines, homopiperazines and corresponding salts according to claim 1, wherein the pair (n,R) takes the value (1,H) and Ar represents a benzimidazolyl-4(7), benzotriazolyl-4(7), indolyl-4 or indolyl-7 group.

3. The piperazines, homopiperazines and corresponding salts according to claim 1, wherein Ar is a benzimidazolyl-4(7) nucleus and the pair (R,n) takes on any one of the values selected from:

(H, 1), (COCH$_3$, 1),

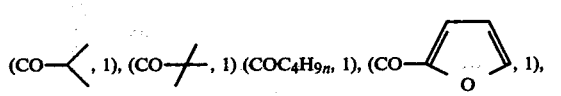

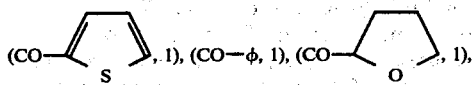

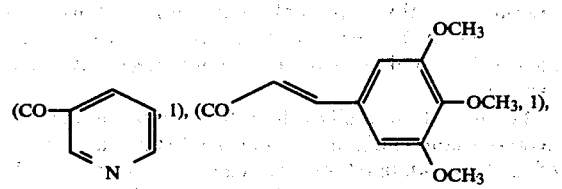

(COOEt, 1), (COOEt, 2), (COOCH$_3$, 1), (COO⁓, 1), (COO⁓, 1), (COO⁓, 1), (COOC$_4$H$_9$, 1), (COO⁓, 1), (COO⁓, 1), (COO⁓φ, 1), (COOO, 1), (SO, 1).

4. A medicament exhibiting antihypertensive activity, formed by one of the compounds or pharmaceutically acceptable salts according to claim 1.

5. An antihypertensive pharmaceutical composition comprising, as active ingredient(s), at least one medicament according to claim 4, in association with a pharmaceutically acceptable support.

6. A compound according to claim 1 wherein n=1; R is a 2-thienylcarbonyl group; and Ar is a benzimidazolyl-4(7) group.

7. A compound according to claim 1 wherein n=1; R=H; and Ar is an indoyl-7 group.

8. (Carbethoxy-4 piperazino-1)-4(7) benzimidazole, maleate.

9. (Piperazino-1)-4(7) benzimidazole, tribromhydrate.

* * * * *